US006540997B1

(12) United States Patent
Sinnott

(10) Patent No.: US 6,540,997 B1
(45) Date of Patent: Apr. 1, 2003

(54) SHELF-STABLE, VIRULENT PREPARATION CONTAINING AGROBACTERIUM CELLS, AN ACIDULANT AND A PHENOLIC COMPOUND

(76) Inventor: Robert A. Sinnott, 3191 W. Drake St., Chandler, AZ (US) 85246-6598

( * ) Notice: Subject to any disclaimer, the term of this patent is extended or adjusted under 35 U.S.C. 154(b) by 0 days.

(21) Appl. No.: 09/491,158

(22) Filed: Jan. 26, 2000

Related U.S. Application Data

(60) Provisional application No. 60/117,460, filed on Jan. 26, 1999.

(51) Int. Cl.$^7$ .................. A01N 25/00; A01N 63/00; C12N 1/00; C12N 1/12; C12N 1/20
(52) U.S. Cl. .................. 424/93.4; 424/405; 435/252.1; 435/822
(58) Field of Search ................. 424/93.1, 405, 424/93.4; 514/701; 435/252.1, 822

(56) References Cited

U.S. PATENT DOCUMENTS

| | | | | |
|---|---|---|---|---|
| 5,981,837 A | * | 11/1999 | Chapple | 800/278 |
| 6,143,543 A | * | 11/2000 | Michelsen et al. | 435/196 |
| 6,251,951 B1 | * | 6/2001 | Emerson et al. | 514/701 |

* cited by examiner

*Primary Examiner*—David M. Naff
*Assistant Examiner*—Deborah K. Ware
(74) *Attorney, Agent, or Firm*—David K. Benson

(57) ABSTRACT

A virulent preparation of Agrobacterium cells, includes Agrobacterium cells, an acidulant, and a phenolic compound that is preferably ethyl vanillin. A method of preparing the preparation includes the steps of preparing a suspension of Agrobacteria in a liquid desiccation medium which includes an acidulant and the phenolic compound and dehydrating the suspension. The preparation is shelf stable at ambient temperature for several months. The preparation may further contain a dry excipient material, a food coloring agent, a flow agent, a plant hormone, a bacterial growth promoter and an antifungal agent.

12 Claims, No Drawings

SHELF-STABLE, VIRULENT PREPARATION CONTAINING AGROBACTERIUM CELLS, AN ACIDULANT AND A PHENOLIC COMPOUND

This application claims the benefit of U.S. Provisional Patent Application No. 60/117,460 filing date Jan. 26, 1999.

FIELD OF THE INVENTION

The present invention relates to the field of preparation and storage of viable Agrobacterium cultures.

BACKGROUND OF THE INVENTION

The preservation of dried microorganisms has present application in such areas as pharmaceuticals and agriculture. Furthermore, research of such organisms is greatly benefited by technology that allows for their long-term preservation. Also, the potential benefits of such preserved microorganisms is great, since dried microorganisms may be stored for long periods of time while retaining significant viability. Freeze-drying is, by far, the most common method employed to prepare dried microorganisms. However, freeze-dried bacteria generally require long-term storage at refrigerated or frozen temperatures to maintain optimum viability. Additionally, freeze-drying requires expensive, specialized equipment. Freeze-drying is also not the optimum method for preparing at least some types of bacterial cultures for storage.

P. Louis et al., *Survival of Escherichia Coli During Drying and Storage in the Presence of Compatible Solutes*, 41 Appl. Microbiol. Biotechnol. at 684 (1994) discloses the use of compatible solutes, small, highly water-soluble organic molecules, and air-drying for preservation of other gram-negative bacterial species, including *Escherichia coli*. These air-dried cultures of *Escherichia coli* are quite stable for several months with out requiring freezing to preserve bacterial cell viability.

Agrobacterium, a genus of gram-negative bacteria, is commonly found in soil and some strains can be plant pathogens. One species of Agrobacterium is *Agrobacterium tumefaciens*, which is the causative agent of crown gall tumors in plants. Another species, *Agrobacterium rhizogenes* is the causative agent of hairy root disease in plants. Both Agrobacterium species, *tumefaciens* and *rhizogenes*, can potentially cause tumor-like growth dysfunction in plants by transferring foreign bacterial genes into plant cells. The ability of Agrobacterium to transfer foreign DNA into plant cells has made Agrobacterium strains very useful vectors for foreign gene transfer into plants in the process known as plant genetic engineering. Additionally, infective virulence of Agrobacterium may be significantly enhanced by treating the Agrobacterium cultures with phenolic compounds, which may be produced by plants in response to wounding, and acidic environmental conditions, such as those found inside some plant tissues. M. Limami et. al., *Natural Genetic Transformation by Agrobacterium rhizogenes*, 118 Plant Physiol. at 543 (1998), J. Porter, *Host Range and Implications of Plant Infection by Agrobacterium Rhizogenes*, 10 Critical Reviews In Plant Sciences, vol. 4, at (1991), H. Matthews et. al., *The Promotion of Agrobacterium Mediated Transformation in Atropa Belladona L. by Acetosyringone*, 136 J. Plant Physiol. at 404 (1990), S. Turk et. al., *Localization of the VirA Domain Involved in Acetosyringone-mediated Vir Gene Induction in Agrobacterium Tumefaciens*, 25 Plant Molecular Biol. at 899 (1994).

There is a great need for a preparation of Agrobacterium that can be conveniently stored at room temperature for an extended period of time since it has great potential utility in agricultural biotechnology research. Such cultures can be transported and stored without the need for refrigeration or freezing. Such handling efficiency would make the use of Agrobacterium under actual field conditions much more practical. There is also a need for a room temperature-stable preparation of Agrobacterium for the preparation of plant biotechnology educational kits. These kits could be displayed in conventional retail settings with extended shelf life. Additionally, there is a need for a process for enhancing Agrobacterium virulence, and to incorporate the process into a method for preserving Agrobacterium preparations. The process would have enhanced utility for routine genetic transformation of plants.

SUMMARY OF THE INVENTION

It is an object of the present invention to meet the above-described needs and others. Specifically, it is an object of the present invention to provide a virulent preparation of Agrobacterium, and a method for making the same. The method may include the step of growing Agrobacterium either in a liquid media, i.e., nutrient broth, or on solid bacteriological media, i.e., nutrient agar, to a stationary growth phase. The method may also include the step of harvesting the grown bacteria by centrifugation.

The method includes the step of suspending bacteria in an Agrobacterium desiccation medium. The Agrobacterium desiccation medium may be an aqueous solution that includes an osmoprotectant that may be approximately 625 millimolar sucrose, an acidulant that may be 50 millimolar sodium dihydrogen phosphate ($NaH_2PO_4$), and a phenolic compound that may be 100 micromolar ethyl vanillin. Other natural or synthetic phenolic compounds may be used with or in place of the micromolar ethyl vanillin such as, sinapyl alcohol, coniferyl alcohol, sinapic acid, sinapic acid methyl ester, sinapinic acid, syringic acid, syringaldehyde, p-hydroxybenzoic acid, vanillalacetone, vanillin, ferulic acid, ferulic acid methyl ester, 5-hydroxyferulic acid methyl ester, flavonoids, lignins, lignans, and acetosyringone. In a preferred embodiment of the invention, the phenolic compound is micromolar ethyl vanillin.

Approximately one gram weight, or one milliliter volume, of bacterial cells per 2 milliliters of the Agrobacterium desiccation medium may be used to prepare the bacterial suspension. After the bacterial cells have been suspended in the aqueous solution, the cell suspension may be dried immediately or stored refrigerated until processing is desired.

The method includes the step of dehydrating the bacteria, which may be performed by slowly air drying the bacterial suspension at approximately 20 to 25° C. and less than 30% relative humidity. When the bacterial suspension is completely dry, it constitutes a shelf-stable, virulent culture of Agrobacterium.

The bacterial suspension may be conveniently applied to a compatible supporting matrix (i.e. autoclaved toothpicks or cellulose powder) prior to the dehydrating step to facilitate ease of handling or packaging. Additionally, the dried bacterial suspension may be ground and diluted with compatible dry or liquid additives to produce a variety of useful forms of the culture.

One use of these cultures is, for example, educational kits to demonstrate the natural genetic engineering of plants. It is beneficial to incorporate into these educational kits cultures of Agrobacterium that remain viable upon storage at room temperatures since these educational kits may then be stored and displayed for sale with other ordinary merchandise in a retail store setting rather than requiring special handling such as refrigerated shipping and storage.

It is a further object of the present invention to provide a virulent preparation of Agrobacterium cells, which includes Agrobacterium cells, an acidulant, and a phenolic compound. The phenolic compound is preferably ethyl vanillin. However, the phenolic compound can be at least one of the following compounds: ethyl vanillin, sinapyl alcohol, coniferyl alcohol, sinapic acid, sinapic acid methyl ester, sinapinic acid, syringic acid, syringaldehyde, p-hydroxybenzoic acid, vanillalacetone, vanillin, ferulic acid, ferulic acid methyl ester, 5-hydroxyferulic acid methyl ester, flavonoids, lignins, lignans, and acetosyringone.

The virulent preparation of Agrobacterium according to the invention can include sodium dihydrogen phosphate as the acidulant.

It is a primary objective that the preparation is shelf stable at ambient temperature for a plurality of months. The preparation as described above accomplishes this objective.

At least one dry excipient material can be included in the virulent preparation of Agrobacterium. A food coloring agent can also be added. At least one flow agent may be included in the preparation, as well as a plant hormone and/or a bacterial growth promoter. Additionally, a fungicidal compound (i.e. myclobutanil or miconazole) may be included in the preparation to prevent fungal infection at the site of plant inoculation with Agrobacterium.

Additional objects, advantages and novel features of the invention will be set forth in the description which follows or may be learned by those skilled in the art through reading these materials or practicing the invention. The objects and advantages of the invention may be achieved through the means recited in the attached claims.

To achieve these stated and other objects, the present invention may be embodied and described as set forth in the detailed description of the preferred embodiments, and in the following claims.

DETAILED DESCRIPTION OF THE PREFERRED EMBODIMENTS

The preferred embodiments of the present invention will now be explained.

First, a primary culture of Agrobacterium, i.e., *Agrobacterium rhizogenes* strain ATCC 15834, obtained from the American Type Culture Collection, Reston, Va., is started from a freeze-dried stock culture. The culture can be started by rehydrating the freeze-dried culture with approximately 1 ml of liquid nutrient media. An example of liquid nutrient media contains approximately: 5 grams of Pancreatic Digest of Gelatin or Peptone, 3 grams of Beef Extract, 0.2 grams of Magnesium Sulfate, and 1 gram of Glucose or 5.0 grams of Sucrose, adjusted to approximately pH 6.8 to 7.2. Nutrient agar contains all the ingredients of nutrient broth with the addition of agar to solidify the media into a semi-solid gel.

The liquid nutrient broth is then sterilized by autoclaving the media for 15 minutes at 15 pounds pressure at 121° C. The media is then allowed to cool to room temperature prior to use. The nutrient agar is sterilized by autoclaving the media for 15 minutes at 15 pounds pressure at 121° C. The media is again allowed to cool to approximately 50° C., and is then transferred into sterile culture dishes. The nutrient agar is allowed to solidify and cool to room temperature prior to use.

The one milliliter of bacterial suspension is added to an additional nine milliliters of nutrient media in a sterile culture tube to make a final volume of 10 milliliters. These ten milliliters of inoculated liquid nutrient media is incubated at 25° C. with gentle agitation for twenty-four hours. This culture of Agrobacterium is then used to inoculate either fresh liquid nutrient media for growing liquid cultures or solid nutrient agar plates for growing solid media cultures.

To produce large volume liquid cultures of Agrobacterium, the twenty-four hour cultures as described above are used to inoculate flasks containing one liter of nutrient media. To initiate the cultures, the liter of fresh nutrient media is inoculated with one milliliter of the twenty-four hour culture. The one-liter cultures are grown to stationary phase, which takes 48 to 168 hours at room temperature (about 25° C.) with gentle agitation of the flasks using an orbital motion platform. At stationary growth phase, the bacterial cells are no longer actively growing, all the cells are essentially at the same stage of development and the bacterial cells have a high degree of cell stability that facilitates further processing steps. The liquid cultures of Agrobacterium are centrifuged to sediment the bacterial cells. The spent media supernatant is removed and the mass of the wet bacterial cells is taken.

To produce large volume cultures of Agrobacterium on nutrient agar plates, the twenty-four hour cultures described above are used to inoculate several sterile petri plates containing nutrient agar. The plates are incubated at room temperature until a thick bacterial lawn forms on the plates. Such formation may take between approximately forty-eight and approximately one hundred sixty eight hours. The bacteria are harvested from the plate by scraping the plates with a sterile spatula and collecting the bacterial cells into a sterile tube. After scraping the plates, they may be incubated at room temperature for an additional period of time until another thick bacterial lawn forms again. Using plates in this way and employing aseptic handling techniques, several harvests may be made from the same plates with a single inoculation. After harvesting from liquid media or from nutrient agar plates, the bacterial cells are then resuspended in an aqueous solution. An example of the solution contains approximately: 625 millimolar sucrose, 50 millimolar sodium dihydrogen phosphate ($NaH_2PO_4$), and 100 micromolar ethyl vanillin. The sucrose acts as an osmoprotectant to protect the bacterial cells during the subsequent desiccation step. The sodium dihydrogen phosphate acts as an acidulant to adjust the pH of the bacterial cells to that of a slightly acidic environment. The acidic environment initiates the induction of virulence genes (Vir genes) in the Agrobacterium cells. Numerous other acidulants or acidic buffers in common use may be used in place of sodium dihydrogen phosphate to stabilize the pH of the media between 4 and 7. Ethyl vanillin, a phenolic compound similar to those found in plant cells, acts to promote the induction of the Vir genes in the bacterial cells. Other natural or synthetic phenolic compounds may be used with or in place of the micromolar ethyl vanillin such as, sinapyl alcohol, coniferyl alcohol, sinapic acid, sinapic acid methyl ester, sinapinic acid, syringic acid, syringaldehyde, p-hydroxybenzoic acid, vanillalacetone, vanillin, ferulic acid, ferulic acid methyl ester, 5-hydroxyferulic acid methyl ester, flavonoids, lignins, lignans, and acetosyringone. In a preferred embodiment of the invention, the phenolic compound is micromolar ethyl vanillin.

Induction of the Vir genes of Agrobacterium by an acidic environment and the presence of phenolic compounds causes the Agrobacterium to more readily infect and genetically transform plant cells that are exposed to such bacteria.

Whether the cells are harvested by centrifugation from liquid cultures or harvested by scraping from solid media cultures, approximately one gram of bacterial cells per 2 milliliters of aqueous solution can be used to prepare the bacterial resuspension.

The bacterial resuspension described above is slowly air dried at approximately 20 to 25 degrees C. and less than 30% relative humidity. If ambient relative humidity is above 30%, the use of a desiccator and a desiccant, such as calcium chloride may be necessary. When the bacterial suspension is completely dry it represents a shelf-stable preparation of Agrobacterium that may be stored at ordinary room temperature and retain viability for several months. Additionally, the bacterial resuspension may be applied to supporting media before drying, such as by dipping the tip of autoclaved toothpicks into the bacterial resuspension and then drying the bacterial resuspension on the toothpick. The use of supporting matrices can be used to facilitate the handling and packaging of the dried bacterial suspension.

The dry culture may be mixed with compatible, dry excipient materials to enhance the properties of the cultures for specialized purposes. For example, food coloring agents or dyes might be used to visually enhance the material to facilitate application to plants. Flow agents such as silica and diatomaceous earth might be used to enhance the physical properties of the dried culture and to reduce clumping of bacterial cells. Plant hormones (i.e. auxins, cytokinins, gibberellins) or bacterial growth promoters could be added to enhance the plant transformation effects of the Agrobacterium infection. Anti-fungal agents (i.e. myclobutanil or miconazole nitrate) might be used to suppress potential fungal infections at the site of inoculation with Agrobacterium.

EXAMPLE #1

Two Agrobacterium cultures (*Agrobacterium rhizogenes* ATCC Strain 15834) were grown in 125 mililiters of Nutrient Broth (5.0 g/L pancreatic digest of gelatin, 3.0 g/L beef extract, 0.2 g/L magnesium sulfate and 1.0 g/L glucose, pH 6.87) at 20 to 25 degrees Celsius with gentle agitation on an orbital platform. One culture was harvested at 96 hours and the other culture was harvested at 168 hours. In both cases, the culture media was centrifuged in a clinical centrifuge for 10 minutes using 15 milliliter sterile plastic culture tubes. The supernatant was discarded and the pellets were combined and resuspended in Agrobacterium Desiccation Medium (625 millimolar sucrose, 50 millimolar sodium dihydrogen phosphate ($NaH_2PO_4$), and 100 micromolar ethyl vanillin). Approximately one gram of bacterial cells per 2 milliliters of aqueous solution were used to prepare the bacterial resuspension. The bacterial resuspension was refrigerated for 72 hours at 5 degrees Celsius before further processing. The tips (approximately 5 millimeters) of sterile, autoclaved wood toothpicks were immersed in the bacterial suspension for 10 minutes. The toothpicks were placed on a sheet of autoclaved aluminum foil and placed in a desiccator containing Drierite as a desiccant. After remaining in the desiccator for 6 hours at room temperature (20 to 25 degrees Celsius), the bacterial suspension applied to the tip of the toothpicks appeared to be dry and was dry to the touch. The treated and dried toothpicks were stored in sterile aluminum foil at room temperature until used for inoculating plant tissues.

EXAMPLE #2

The treated and dried toothpicks prepared in Example #1 were used to inoculate plant tissues by piercing parts of an intact, healthy plant stem (Petunia) with the tip of the toothpick treated with the bacterial suspension. The toothpick was allowed to remain in place inside the plant tissue for approximately one week, during which time the inoculated plant was grown under high humidity. The plant was then returned to its normal environment and monitored for symptoms of Agrobacterium infection.

It is considered that a strong advantage of the present invention is the ability of the dried cultures to be included in educational kits for demonstrating the natural genetic engineering of plants. It is of great benefit that such educational kits can incorporate cultures of Agrobacterium that remain viable upon storage at room temperatures since these educational kits may then be stored and displayed for sale with other ordinary merchandise in a retail store setting rather than requiring special handling such as refrigerated shipping and storage.

The preceding description has been presented only to illustrate and describe the invention. It is not intended to be exhaustive or to limit the invention to any precise form disclosed. Many modifications and variations are possible in light of the above teaching.

The preferred embodiment was chosen and described in order to best explain the principles of the invention and its practical application. The preceding description is intended to enable others skilled in the art to best utilize the invention in various embodiments and with various modifications as are suited to the particular use contemplated. It is intended that the scope of the invention be defined by the following claims.

What is claimed is:

1. A virulent preparation of Agrobacterium cells, which comprises:
    said Agrobacterium cells;
    an acidulant; and
    a phenolic compound,
    wherein said preparation is shelf stable at ambient temperature for a plurality of months.

2. A virulent preparation of Agrobacterium cells as set forth in claim 1, wherein said phenolic compound is ethyl vanillin.

3. A virulent preparation of Agrobacterium cells as set forth in claim 1, wherein said phenolic compound is at least one compound selected from the group consisting of ethyl vanillin, sinapyl alcohol, coniferyl alcohol, sinapic acid, sinapic acid methyl ester, sinapinic acid, syringic acid, syringaldehyde, p-hydroxybenzoic acid, vanillalacetone, vanillin, ferulic acid, ferulic acid methyl ester, 5-hydroxyferulic acid methyl ester, flavonoids, lignins, lignans, and acetosyringone.

4. A virulent preparation of Agrobacterium cells as set forth in claim 1, wherein said adiculant is sodium dihydrogen phosphate.

5. A virulent preparation of Agrobacterium cells as set forth in claim 1, which further comprises at least one dry excipient material.

6. A virulent preparation of Agrobacterium cells as set forth in claim 1, which further comprises a food coloring agent.

7. A virulent preparation of Agrobacterium cells as set forth in claim 1, which further comprises at least one flow agent.

8. A virulent preparation of Agrobacterium cells as set forth in claim 1, which further comprises a plant hormone.

9. A virulent preparation of Agrobacterium cells as set forth in claim 1, which further comprises a bacterial growth promoter.

10. A virulent preparation of Agrobacterium cells as set forth in claim 1, which further comprises an anti-fungal agent.

11. A virulent preparation of Agrobacterium cells as set forth in claim 1, wherein said preparation is dried.

12. A virulent preparation of Agrobacterium cells as set forth in claim 1, which further comprises a dry supporting medium.